United States Patent [19]

Eldridge et al.

[11] Patent Number: 5,361,641
[45] Date of Patent: Nov. 8, 1994

[54] APPARATUS FOR PERFORMING HIGH-TEMPERATURE FIBER PUSH-OUT TESTING

[75] Inventors: Jeffrey I. Eldridge, Rocky River; Ben T. Ebihara, Strongsville, both of Ohio

[73] Assignee: The United States of America as represented by the Administrator of the National Aeronautics and Space Administration, Washington, D.C.

[21] Appl. No.: 968,087

[22] Filed: Dec. 21, 1992

[51] Int. Cl.⁵ .............................................. G01N 3/42
[52] U.S. Cl. ................................................ 73/842
[58] Field of Search .......... 73/841, 842, 845, 826–828, 73/830; 374/46, 49, 50; 392/347, 355

[56] References Cited

U.S. PATENT DOCUMENTS

| | | |
|---|---|---|
| 2,892,342 | 6/1959 | Goss et al. |
| 3,176,499 | 4/1965 | Sikora ........................... 374/50 |
| 3,795,134 | 3/1974 | Eichenbrenner et al. ...... 73/15.6 |
| 4,537,060 | 8/1985 | Underwood ................... 73/12 |
| 4,627,287 | 12/1986 | Suga ............................. 73/865.6 |
| 4,662,228 | 5/1987 | Tse ................................ 73/842 |
| 4,841,779 | 6/1989 | Mitsuhashi et al. ........... 73/826 |
| 4,926,118 | 5/1990 | O'Connor et al. ............. 324/128 |
| 4,972,720 | 11/1990 | Wu ................................ 73/801 |

OTHER PUBLICATIONS

Kozub et al., "Universal Chamber For High Temperature Mechanical Testing up to 2000° C.", INSPEC, Jul. 1976.
Kaplan, "A temperature stabilization system for a vacuum test machine", Feb. 1976.

*Primary Examiner*—Robert Raevis
*Attorney, Agent, or Firm*—Gene E. Shook; Guy M. Miller

[57] ABSTRACT

The apparatus disclosed in the present invention measures the force at which a fiber resist the motion of an indenter driven at constant speed. This apparatus conducts these test in a vacuum of about $10^{-6}$ tort and at temperatures up to 1100° C. Temperature and vacuum environment are maintained while controlling indenter motion, sample position, and providing magnified visual inspection during the test.

15 Claims, 2 Drawing Sheets

APPARATUS FOR PERFORMING HIGH-TEMPERATURE FIBER PUSH-OUT TESTING

ORIGIN OF THE INVENTION

The invention described herein was made by employees of the United States Government and may be manufactured and used by or for the Government for governmental purposes without the payment of any royalties thereon or therefore.

FIELD OF THE INVENTION

The present invention is directed to a method of testing the mechanical strength of the interface between a reinforcing fiber and the surrounding matrix material.

The interfacial behavior of a fiber reinforced composite is important because interfacial strength has a significant impact on the overall strength and toughness of the composite material. Various models have been proposed which relate the mechanical properties of the interface to those of the composite. As a result, fiber push-out testing has become an important tool for characterizing fiber debonding and sliding behavior in fiber-reinforced composite materials.

Because the target use of many of the composite materials is at elevated temperatures, it is beneficial to extend the measuring range of interfacial testing to elevated temperatures, such as 1100° C.

It is, therefore, an object of the present invention to perform fiber push-out testing at elevated temperatures.

It is a further object of this invention to generate data at composite service temperatures which could be used to optimize interfacial mechanical behavior while minimizing specimen oxidation at those elevated temperatures.

It is another object of the present invention to evaluate the effects of residual stresses on fiber debonding and sliding.

It is still a further object of the invention to maintain a magnified line-of-sight with the specimen during loading, so that the test can be monitored visually.

It is still another object of the invention to determine the force at which a fiber resists the motion of an indenter driven at a constant displacement rate at elevated temperatures.

DESCRIPTION OF THE RELATED ART

Gass U.S. Pat. No. 2,892,342 is directed to a test apparatus which is used to determine the force necessary to induce failure in a plastic material. Eichenbrenner U.S. Pat. No. 3,795,134 is directed to a means of testing a metal specimen under conditions of heating. Underwood U.S. Pat. No. 4,537,060 discusses an apparatus including a cam driven flywheel which applies mass to a subject material. Suga U.S. Pat. No. 4,627,287, shows a xenon lamp, a focusing reflector, an air cooling means, and an arrangement which allows for the uniform heating of a specimen along the surface of a test structure.

Tse U.S. Pat. No. 4,662,228 relates to a fiber push-out apparatus. O'Connor U.S. Pat. No. 4,926,118 describes a mechanism for testing materials in a heating environment. Wu U.S. Pat. No. 4,972,720 is directed to a method and apparatus for the thermal testing of composite materials in which heat applied to the subject causes it to deform.

SUMMARY OF THE INVENTION

The present invention is directed to an apparatus for performing push-out testing of a fiber reinforced matrix composite. An evacuated chamber is provided for heating a composite and an indenter by focusing the radiation from a halogen lamp through a quartz window onto the composite specimen and indenter. While the specimen temperature is remotely monitored through a thermocouple, a nearby remotely controlled translation stage used for sample positioning is maintained near room temperature by a water cooled copper plate underneath a heat isolating platform.

During the testing a microscope connected to a television camera provides high-resolution remote monitoring on a television monitor. Alignment of the indenter and fiber is achieved by visually positioning the sample through a remotely controlled motorized translational stage inside the test chamber. Correct alignment is evaluated by visual inspection of the magnified image on the television monitor. Controlled indenter displacement inside the test chamber is performed using a linear motion feedthrough driven by a stepper motor outside the test chamber. A load cell connected to a displacement shaft inside the test chamber enables monitoring of the load applied to the composite specimen by sending electrical signals corresponding to the load through a data acquisition system, to a remote computer.

BRIEF DESCRIPTION OF THE DRAWINGS

The advantages and novel features of the invention will be more fully apparent from the following detailed description when read in connection with the accompanying drawings in which.

DESCRIPTION OF THE PREFERRED EMBODIMENT

Figure 1:
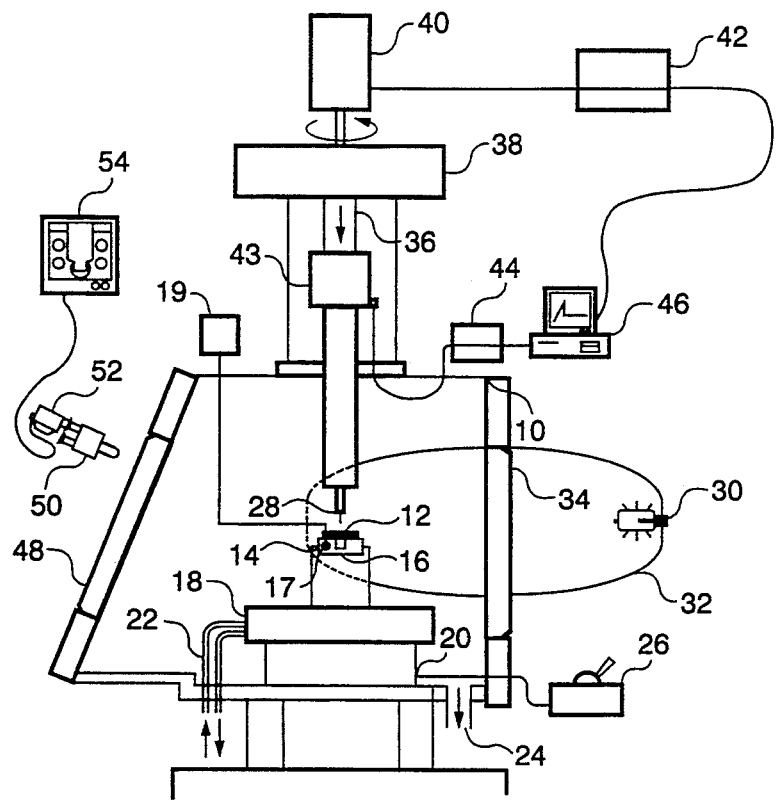
FIG. 1 is a schematic view of the high temperature fiber push-out apparatus.

A schematic view of a fiber push-out apparatus is shown in FIG. 1. In the apparatus a cubical stainless steel chamber 10 with conflat-flanged ports on each face, houses a composite specimen 12. The specimen is supported by a sample support block 14 which has a set of three 300 $\mu$m diameter grooves 16 underneath the sample 12 which allows the fibers to be pushed out without resistance from the support block. The sample and support block are spring-clamped to a heat isolating platform consisting of a machineable ceramic cylinder on top of a hollow stainless steel base. Underneath the heat isolating platform is a copper plate 18 cooled by water through pipes 22 which keeps the transitional stage 20 near room temperature. A turbopump exit area 24 facilitates the evacuation of the chamber, producing an inert environment. The inert environment facilitates the heating of the specimen without oxidation. The translational stage is controlled remotely through a joystick controller 26, enabling the specimen 12 to be placed under an indentor 28 for pushout testing.

Both the specimen 12 and the indentor 28 are heated by a quartz halogen lamp 30. A radiant energy heating system composed of a two piece ellipsoidal reflector 32, focuses the radiant energy generated by the lamp 30 onto the specimen 12 and indentor. The reflector is bisected by a quartz window halfway between the two focal points of the reflector. Bisecting the reflector places half of the reflector inside the chamber and the other half outside. The halogen lamp is in the portion of the reflector outside of the chamber enabling conventional cooling of the lamp by forced air convection. The quartz window 34 allows maximum transmission of the heating radiation produced by the halogen lamp. As a result, the quartz window 34 does not impede the quick heating of the specimen 16. A temperature sensing means 17 displays the temperature to an outside display 19. Sample temperatures as high as 1100° are attained within 10 minutes.

When preparing for a test a thin slice of a fiber reinforced composite is polished to smooth and expose the fiber ends in the matrix. A specific fiber is then indexed for fiber push-out testing.

In the testing apparatus a flat-bottomed cylindrical tungsten carbide punch with a diameter of 100 $\mu m$ is used for pushing out a 142 $\mu m$ diameter SCS-6 SiC fiber. The indenter 28 was attached by a shaft 36 to a linear motion feed-through 38 which enables the control of the indenter from outside the chamber. The commercially available vacuum linear motion feedthrough was modified by the addition of a teflon bushing around the shaft entering the Vacuum as well as the addition of two thrust washers around the threaded shaft entering the feedthrough from the atmosphere side. These modifications eliminated both vertical and lateral play in the shaft that made the performance of the feedthrough unacceptable in its unmodified form. The linear motion feed-through 38 is driven by a stepper motor 40 which provides controlled loading by a computer 46, of the indenter 28 onto the specimen 12. The computer 46 is connected to the stepper motor 40 through a motor controller 42. The motor controller 42 facilitates the uniform loading of the indenter onto the specimen and automatic retraction of the indenter at the completion of a test.

During a typical test the stepper motor shaft rotated at 0.1 rpm (50,800 microsteps/rev) which translates to 1.06 $\mu m/s$ linear motion of the indenter. A load cell 43 attached between the shaft 36 and the indentor 28 produces and electrical signal proportional to the applied load which is collected by a data acquisition system 44. The information is then transferred to the computer 46 which collects stores and analyzes the raw data.

A quartz window 48 tilted at 25° from the vertical so that the window is perpendicular to the line of sight, minimizes the image distortion and reflections that can be caused by a viewing window. A long working distance optical microscope 50 is positioned facing the quartz window 48, to enable a continuous line of sight view while positioning and testing the specimen. An enlarged view of the specimen and indentor can be viewed remotely at a television monitor 54 which is connected to a television camera 52 attached to the microscope 50.

Figure 2:
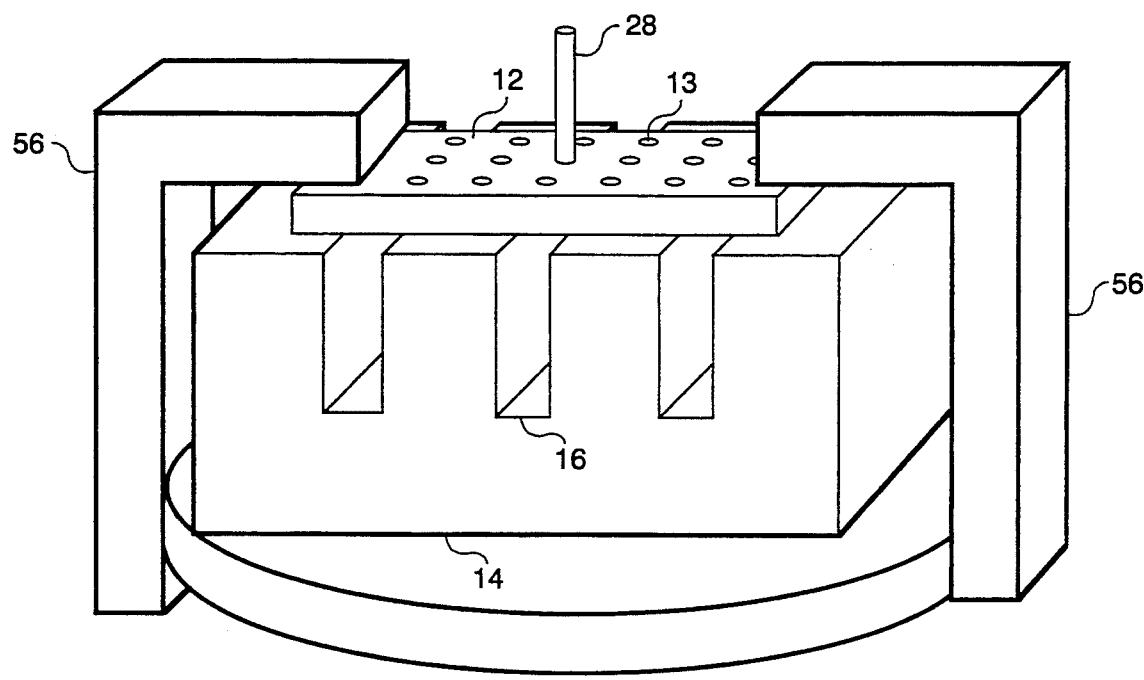
FIG. 2 shows an enlarged view of the sample in the push-out apparatus.

FIG. 2 displays an enlarged view of the specimen 12 displaying the orientation of the fibers 13 a spring-loaded clamp (56) eliminates the need for any type of adhesive or glue. The sample clamp 56 secures the specimen in place against the support block 14. The fibers to be tested 13 are aligned above the 300 $\mu m$/width grooves 16 so that there is no resistance by the support block 14 when a fiber is pushed out by the indentor 28.

Figure 3:
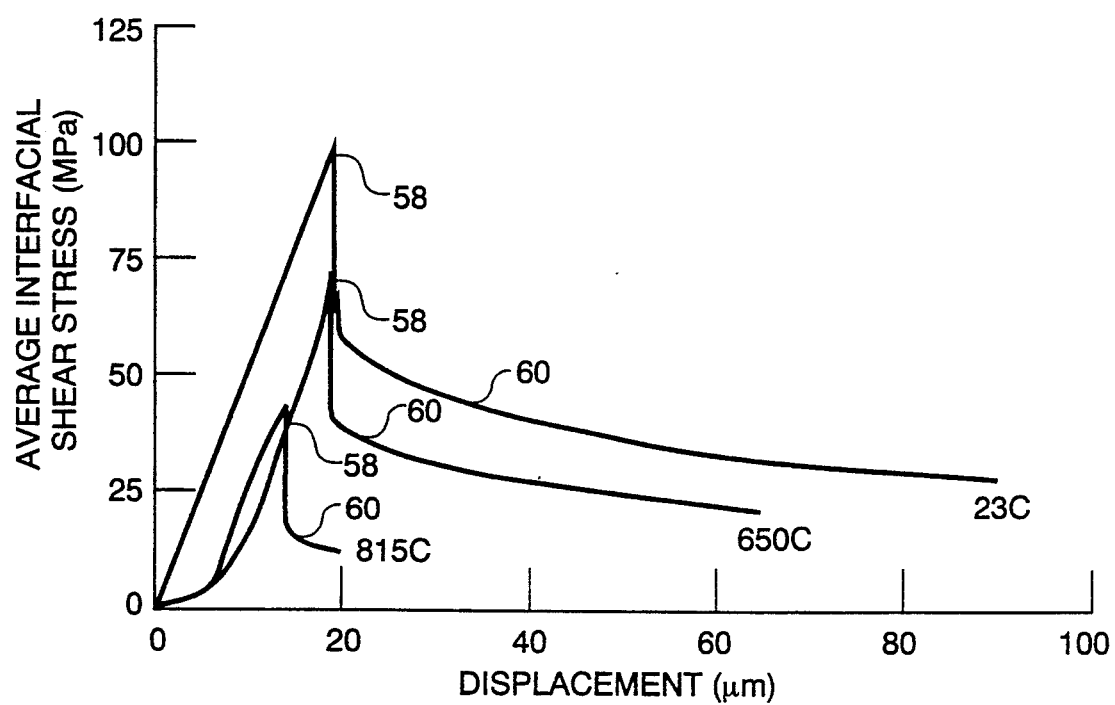
FIG. 3 shows fiber push-out stress/displacement curves at different temperatures for SCS—6 SiC fiber reinforced Ti-24AL-11N6.

FIG. 3 displays a graph of the average interfacial shear stress versus the linear motion feedthrough shaft displacement. A set of graphs are generated for the displacement of SCS-6 SiC fiber at different temperatures in degrees celsius. The debonding of the fiber from the surrounding composite material can be observed at the peaks in the curves 58 and the friction associated with the fiber being pushed out is noted in 60 as the curves flattens out.

While the preferred embodiment of the invention is disclosed and described it will be apparent that various modifications may be made without departing from the spirit of the invention or the scope of the subjoined claims.

What is claimed is:

1. Apparatus for testing high temperature interfacial shear behavior of a fiber within a fiber reinforced composite, said apparatus comprising;

a chamber including a first and a second window for housing said fiber reinforced composite, pumping means for evacuating air from said chamber thereby reducing oxidation of said fiber-reinforced composite, heat sensing means in contact with said fiber-reinforced composite and connected to an outside display device thereby enabling remote temperature measurement during loading of said fiber-reinforced composite, a microscope attached through a television camera to a television monitor facing said second window for maintaining magnified line of sight eye contact with said fiber-reinforced composite at a remote location thereby enabling positioning and monitoring of said fiber-reinforced composite before, during and after loading the fiber in said fiber-reinforced composite, a translational stage supporting a sample support block oriented to allow unincumbered push out of the fiber, said translational stage being connected to a controller outside said chamber whereby remote movement of said translational stage is controlled thereby enabling remote positioning of said fiber-reinforced composite while maintaining said magnified line of sight eye contact, a plate contiguous with said translational stage thereby retarding heating of said translational stage when heating said fiber-reinforced composite, a radiant energy heating system including, a reflector bisected by said first window thereby producing a two-piece reflector having a focal point in each piece of said two piece reflector with said first window serving as a barrier to maintain a vacuum inside said chamber, said first window being positioned so that one piece of said two-piece reflector is outside of said chamber, said one piece outside of said chamber including a lamp located at the focal point of said reflector outside of said chamber, said lamp providing heat whereby focused heating is guided onto the focal point of another piece of the reflector inside the chamber thereby heating said fiber in said fiber-reinforced composite, an indentor mounted above said fiber-reinforced composite for applying a load to said fiber within said fiber-reinforced composite, a shaft connected to said indentor enabling control of vertical loading of said indentor, a load cell attached to said shaft for measuring load applied to said fiber by converting load magnitudes to an electrical signal for interpretation by a computer attached outside of said chamber through a data acquisition device, and a motor driven linear motion feedthrough attached to said load cell for applying constant speed displacement of said indentor thereby enabling push out testing of said fiber within said fiber-reinforced composite.

2. Apparatus as claimed in claim 1 wherein said first and said second windows are made of quartz.

3. Apparatus as claimed in claim 2 wherein said second window is angled perpendicular to the line of sight of said composite specimen thereby reducing image distortion and reflections of said fiber-reinforced composite when viewing said fiber-reinforced composite through said microscope attached through said television camera to said television monitor.

4. Apparatus as claimed in claim I wherein said indentor is smaller in diameter than said fibers in said fiber-reinforced composite thereby enabling push-out of said fiber without the indentor coming in contact with said fiber matrix composite.

5. Apparatus as claimed in claim 1 wherein said fiber-reinforced composite is supported by a sample support block with grooves aligned below said fibers thereby enabling the fibers to be pushed out without resistance from the support block.

6. Apparatus as claimed in claim I wherein said two piece heat focusing reflector is elliptical in shape.

7. Apparatus as claimed in claim 1 wherein said indenter has a flat bottomed cylindrical shape thereby enabling displacement of a fiber within said fiber-reinforced composite without contact between the indenter and the matrix.

8. Apparatus as claimed in claim 1 wherein said pumping means is a turbomolecular pump.

9. An apparatus as claimed in claim 1 wherein a heat isolating means is located between said translational stage and said sample support block thereby isolating heat from said translational stage when heating the fiber in said fiber matrix composite.

10. A high temperature fiber push-out apparatus comprising:

a chamber including a first and a second window for housing a fiber-reinforced composite having fibers therein, a heating means facing said first window for focusing and rapidly heating said fiber-reinforced composite to elevated temperatures, said heating means including a heat radiating lamp enveloped by an ellipsoidal reflector, said reflector focusing heat from said heat radiating lamp through said first window onto said fiber-reinforced composite thereby heating the same, visual monitoring means facing said second window for continually viewing said fiber-reinforced composite when positioning and testing the same, loading means for providing constant speed loading of a fiber within said fiber-reinforced composite thereby performing fiber push out testing, translational means for positioning said fiber-reinforced composite under said loading means while maintaining line of sight eye contact with said fiber-reinforced composite through said visual monitoring means, heat isolating means for isolating heat produced by said heating means from said translational means, a water cooled plate contiguous with said translational means thereby retarding heating of said translational means when heating said fiber-reinforced composite, a radiant energy heating system including, a reflector bisected by said first window thereby producing a two-piece reflector having a focal point in each piece of said two piece reflector with said first window serving as a barrier to maintain a vacuum inside said chamber, said first window being positioned so that one piece of said two-piece reflector is inside of said chamber, and another piece of said two-piece reflector is outside of said chamber, said other piece outside of said chamber including a lamp located at the focal point of said reflector outside of said chamber, said lamp providing heat whereby focused heating is guided onto the focal point of said one piece of the reflector inside the chamber by said two piece reflector thereby heating said fiber in said fiber-reinforced composite, an indenter mounted above said fiber-reinforced composite for applying a load to said fiber within said fiber-reinforced composite, a shaft connected to said indentor enabling control of vertical loading of said indentor, a load cell attached to said shaft for measuring load applied to said fiber by converting load magnitudes to an electrical signal for interpretation by a computer attached outside of said chamber through a data acquisition device, and air evacuating means for evacuating air from said chamber whereby a vacuum is created thereby reducing oxidation of said fiber-reinforced composite and facilitating said rapid heating of said fiber-reinforced composite.

11. A high temperature fiber push-out apparatus comprising;

a chamber including a first and a second window for housing a fiber-reinforced composite having fibers therein, heating means facing said first window for focusing and rapidly heating said fiber-reinforced composite to elevated temperatures, visual monitoring means facing said second window for continually viewing said fiber-reinforced composite when positioning and testing the same, said visual monitoring means include a microscope providing remote monitoring of said specimen through a television camera attached to said microscope and cabled to a television monitor thereby providing continual remote viewing of said fiber-reinforced composite, loading means for providing constant speed loading of a fiber within said fiber-reinforced composite thereby performing fiber push out testing, translational means for positioning said fiber-reinforced composite under said loading means while maintaining line of sight eye contact with said fiber-reinforced composite through said visual monitoring means, heat isolating means for isolating heat produced by said heating means from said translational means, and air evacuating means for evacuating air from said chamber whereby a vacuum is created thereby reducing oxidation of said fiber-reinforced composite and facilitating said rapid heating of said fiber-reinforced composite.

12. Apparatus as claimed in claim 11 wherein said first and said second windows are made of quartz thereby enabling heating and viewing of said composite specimen with minimal reflection and distortion.

13. A method of loading a fiber in a fiber-reinforced composite at elevated temperatures comprising the steps of;

preparing a polished thin slice of said fiber-reinforced composite, exposing individual fiber ends in said fiber-reinforced composite for testing, securing said fiber-reinforced composite on a sample support block where at least one of said individual fiber ends is aligned above a groove in said sample support block, and where said sample support block is secured to a heat isolating platform, securing said sample support block and said heating isolating platform assembly in a chamber on a water cooled plate, said chamber including a first quartz window facing a heating lamp and a second quartz window facing a viewing means, viewing said fiber-reinforced composite from a remote location through a microscope facing the second quartz window, said microscope being connected to a camera connected to a remote monitor thereby enabling remote magnified viewing of said fiber-reinforced composite, positioning said at least one fiber ends in said fiber-reinforced composite under an indentor while viewing by moving a remotely controlled translation stage connected to said water-cooled plate thereby aligning said indentor with said at least one of said individual fiber ends in the fiber reinforced composite, evacuating air from said chamber thereby reducing oxidation of said fiber-reinforced composite and dissipation of heat, providing focused heating of said fiber-reinforced composite through said first quartz window by using an elliptically shaped reflector with said heating lamp therein, monitoring temperature of said fiber-reinforced composite from a remote location through a temperature display device connected to a thermocouple in close proximity to said fiber-reinforced composite, loading said at least one individual fiber ends in said fiber-reinforced composite with said indentor connected through a shaft to a load cell, monitoring the load applied to said at least one individual fiber ends from a remote computer attached to the load cell, and assessing structural failure produced by loading said indexed fiber in the remote computer.

14. A method as claimed in claim 13 wherein evacuating the air from said chamber produces a base pressure below $1 \times 10^{-6}$ torr.

15. A method as claimed in claim 14 wherein said composite specimen is heated to about 1100° C. in about 10 minutes.

* * * * *